(12) United States Patent
Craig et al.

(10) Patent No.: US 10,603,065 B2
(45) Date of Patent: Mar. 31, 2020

(54) SURGICAL INSTRUMENTS AND JAW MEMBERS THEREOF

(71) Applicant: COVIDIEN LP, Mansfield, MA (US)

(72) Inventors: Jason L. Craig, Loveland, CO (US); Kenneth E. Netzel, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 327 days.

(21) Appl. No.: 15/425,544

(22) Filed: Feb. 6, 2017

(65) Prior Publication Data

US 2017/0238959 A1     Aug. 24, 2017

Related U.S. Application Data

(60) Provisional application No. 62/296,942, filed on Feb. 18, 2016.

(51) Int. Cl.
    *A61B 17/32*     (2006.01)
    *A61B 17/28*     (2006.01)
    *A61B 17/00*     (2006.01)

(52) U.S. Cl.
    CPC .... *A61B 17/320092* (2013.01); *A61B 17/282* (2013.01); *A61B 2017/00831* (2013.01); *A61B 2017/2825* (2013.01); *A61B 2017/320072* (2013.01); *A61B 2017/320094* (2017.08)

(58) Field of Classification Search
    CPC .................. A61B 17/28; A61B 17/282; A61B 2017/2825; A61B 17/320092; A61B 2017/00831; A61B 2017/320072
See application file for complete search history.

(56) References Cited

U.S. PATENT DOCUMENTS 3,839,698 A    10/1974   Ehrlich
4,626,728 A    12/1986   Flachenecker et al.
5,643,353 A     7/1997   Wallace et al.
(Continued)

FOREIGN PATENT DOCUMENTS

DE        03507672 A1    9/1986
DE        03630478 C1    1/1988
(Continued)

OTHER PUBLICATIONS

Extended European Search Report corresponding to counterpart Int'l Appln. No. EP 16 15 1211.6, dated May 9, 2016.
(Continued)

*Primary Examiner* — George J Ulsh
(74) *Attorney, Agent, or Firm* — Carter, DeLuca & Farrell, LLP

(57) ABSTRACT

A jaw member for use with a surgical instrument includes a support base, a jaw liner, and a jaw overmold. The support base has a proximal portion configured to be pivotably coupled to a surgical instrument, and a distal portion. The support base defines a channel that extends longitudinally between the proximal and distal portions and an aperture disposed in communication with the channel. The jaw liner includes an elongate body configured for receipt in the channel of the support base, and a projection extending from the elongate body and configured for receipt in the aperture of the support base. The jaw overmold overlaps at least a portion of the support base and the jaw liner to fix the jaw liner to the support base.

20 Claims, 14 Drawing Sheets

(56) References Cited

U.S. PATENT DOCUMENTS

| | | | |
|---|---|---|---|
| 2006/0079879 A1 | 4/2006 | Faller et al. | |
| 2007/0191713 A1* | 8/2007 | Eichmann | A61B 17/1606 600/471 |
| 2012/0110758 A1 | 5/2012 | Kanazawa | |
| 2013/0046337 A1 | 2/2013 | Evans et al. | |
| 2015/0073457 A1 | 3/2015 | Stoddard et al. | |
| 2015/0073458 A1 | 3/2015 | Stoddard et al. | |
| 2015/0148832 A1 | 5/2015 | Boudreaux et al. | |
| 2015/0164532 A1 | 6/2015 | Faller et al. | |
| 2015/0201960 A1 | 7/2015 | Akagane | |
| 2016/0206343 A1 | 7/2016 | Ross et al. | |

FOREIGN PATENT DOCUMENTS

| | | |
|---|---|---|
| DE | 20118698 U1 | 4/2003 |
| DE | 20118699 | 4/2003 |
| DE | 20303776 U1 | 7/2004 |
| JP | 61096419 | 5/1986 |
| JP | 63302699 | 12/1988 |
| JP | 02034008 | 2/1990 |
| JP | 06114069 | 4/1994 |
| JP | 2000237204 A | 9/2000 |
| JP | 2001212514 A | 8/2001 |
| JP | 2001346805 A | 12/2001 |
| JP | 2002045368 A | 2/2002 |
| JP | 2002186901 A | 7/2002 |
| JP | 24254128 | 9/2004 |
| JP | 3696034 B2 | 9/2005 |
| JP | 3756726 B2 | 3/2006 |
| JP | 2012096193 A | 5/2012 |
| WO | 2005/107613 A1 | 11/2005 |
| WO | 2005/122917 A1 | 12/2005 |
| WO | 2007/014183 A2 | 2/2007 |
| WO | 2007014548 A2 | 2/2007 |
| WO | 07047380 A2 | 4/2007 |
| WO | 2014/178436 A1 | 11/2014 |

OTHER PUBLICATIONS

Extended European Search Report dated Jun. 23, 2017, corresponding to European Application No. 17156604.5; 12 pages.
Extended European Search Report dated Aug. 23, 2017, corresponding to European Application No. 17156604.5; 12 pages.

* cited by examiner

SURGICAL INSTRUMENTS AND JAW MEMBERS THEREOF

CROSS REFERENCE TO RELATED APPLICATION

The present application claims the benefit of and priority to U.S. Provisional Application Ser. No. 62/296,942, filed on Feb. 18, 2016, the entire contents of which are incorporated herein by reference.

BACKGROUND

Technical Field

The present disclosure relates to jaw members of surgical instruments and, more particularly, to jaw members of ultrasonic surgical instruments.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue. An ultrasonic surgical instrument is configured to transmit ultrasonic energy produced by a generator and transducer assembly along a waveguide to an end effector that is spaced-apart from the generator and transducer assembly. The end effector includes a blade and a jaw member configured to clamp and treat tissue between the blade and the jaw member.

Typically, the vibrations induced in the blade will be transferred to the jaw member, which may damage the jaw member or other components of the surgical instrument. Additionally, the high frequency vibrations may generate high temperatures in the jaw member, which may also damage the jaw member.

Accordingly, a need exists for an improved jaw member constructed to withstand the high frequency vibrations generated by the ultrasonic surgical instrument and/or to withstand the high temperatures produced thereby.

SUMMARY

In one aspect of the present disclosure, an embodiment of a jaw member for use with a surgical instrument is provided. The jaw member includes a support base, a jaw liner, and a jaw overmold. The support base has a proximal portion configured to be pivotably coupled to a surgical instrument, and a distal portion. The support base defines a channel that extends longitudinally between the proximal and distal portions and an aperture disposed in communication with the channel. The jaw liner includes an elongate body configured for receipt in the channel of the support base, and a projection extending from the elongate body and configured for receipt in the aperture of the support base. The jaw overmold overlaps at least a portion of the support base and the jaw liner to fix the jaw liner to the support base.

In some embodiments, the jaw overmold may include a top surface having a plurality of teeth configured to contact tissue. The jaw liner may have a non-planar tissue-contacting surface, and the top surface of the jaw overmold may be non-planar.

It is contemplated that the projection of the jaw liner may extend through the support base to project from a bottom surface of the support base.

It is envisioned that the jaw liner may have a tissue-contacting surface fabricated from a plastic. The plastic may be selected from the group consisting of polytetrafluoroethylene, polyetheretherketone, perfluoroalkoxy, and fluorinated ethylene propylene.

In some aspects of the present disclosure, the support base may have a top surface, and the jaw liner may have a tissue-contacting surface that projects inwardly from the top surface of the support base.

It is envisioned that the aperture of the support base may be a plurality of longitudinally spaced apertures, and that the projection of the jaw liner may be a plurality of longitudinally spaced projections configured for receipt within a respective one of the apertures.

In some aspects of the present disclosure, the projections of the jaw liner may be mushroom-shaped. The projections may extend laterally from a first side of the elongated body of the jaw liner and a second side of the elongated body of the jaw liner. The support base may define an inner groove configured to capture the projections therein.

In some embodiments, the jaw liner may have a tissue-contacting surface having a plurality of teeth disposed along a length of the jaw liner. The teeth may be arranged in two parallel rows. The tissue-contacting surface of the jaw liner may define a space between adjacent teeth. The space may have a triangular portion and an arcuate portion in communication with the triangular portion.

In another aspect of the present disclosure, a jaw member for use with a surgical instrument is provided and includes a support base, a jaw liner, and a jaw overmold. The support base is configured to be pivotably coupled to a surgical instrument. The jaw liner includes an elongated body and an appendage extending laterally from the elongated body. The elongated body and the appendage are each configured for receipt in the support base. The jaw overmold overlaps at least a portion of the support base and the jaw liner to fix the jaw liner to the support base.

In some embodiments, the jaw liner may have an L-shaped transverse cross-sectional profile.

It is envisioned that the jaw liner may further include a tissue-contacting surface defined on the elongated body and having a width that is greater than a width of the elongated body of the jaw liner.

In yet another aspect of the present disclosure, another embodiment of a jaw member for use with a surgical instrument is provided. The jaw member includes a support base, a jaw liner, and an elongated plate. The support base has a proximal portion configured to be pivotably coupled to a surgical instrument, and a distal portion. The support base defines a channel therein that extends longitudinally between the proximal and distal portions. The jaw liner includes an elongate body and a projection extending radially outward from a periphery of the elongate body. The elongate body is configured for receipt in the channel of the support base, and the projection is configured to be seated within the support base. The plate is configured to be coupled to the support base at a location adjacent the jaw liner to secure the jaw liner relative to the support base.

In some embodiments, the support base may include a stepped portion formed therein. The stepped portion may define a first ledge configured to receive the projection, and a second ledge configured to receive the plate. The support base may have an outer surface that extends over the second ledge such that the plate is captured between the outer surface of the support base and the second ledge of the support base.

It is contemplated that the elongate body of the jaw liner may have a distal portion, and that the distal portion of the support base may define a notch therein configured for receipt of the distal portion of the jaw liner to resist distal movement of the jaw liner relative to the support base.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1A:
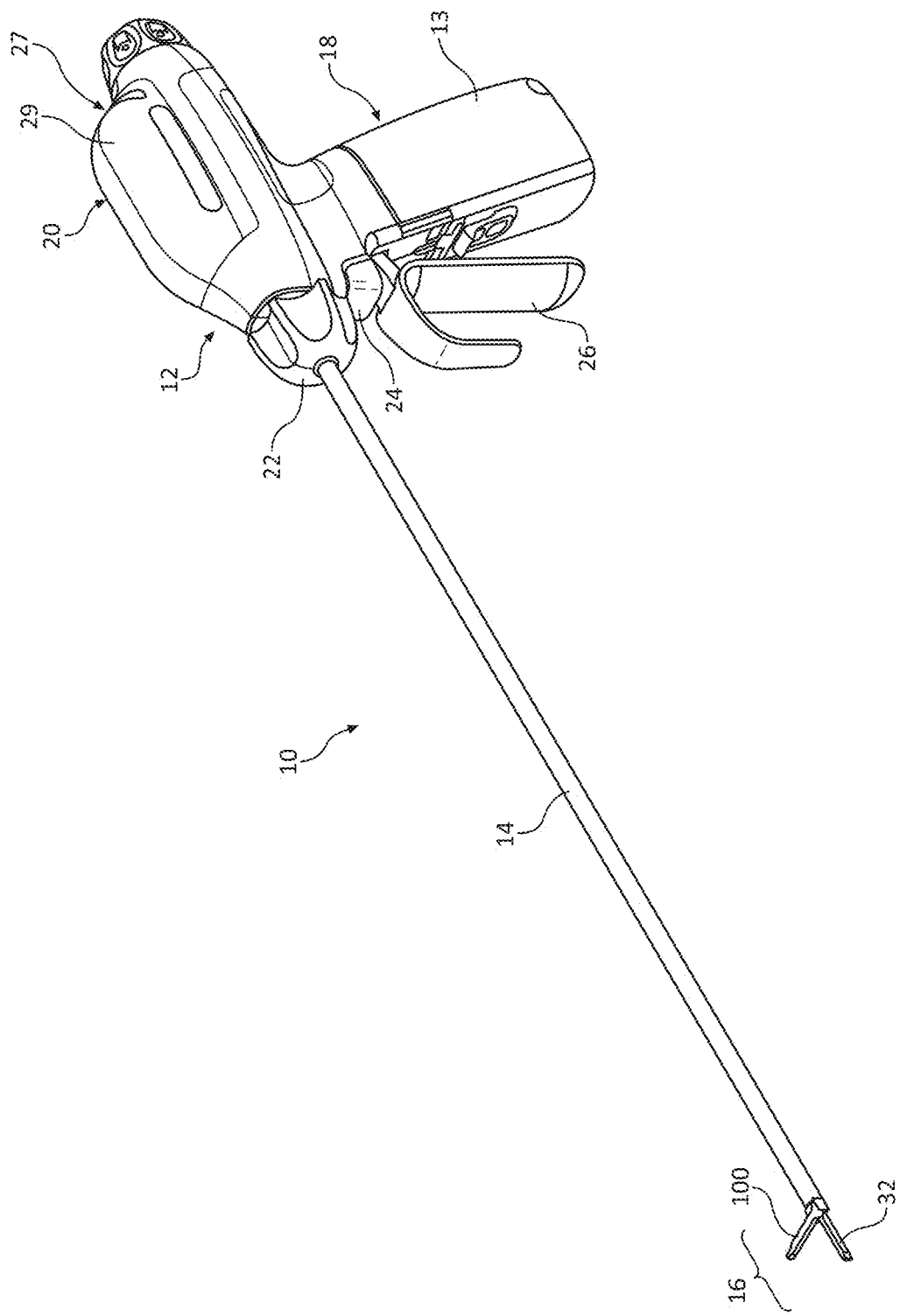
FIG. 1A is a perspective view of an ultrasonic surgical instrument provided in accordance with the present disclosure, including a tool assembly thereof illustrated in an open condition.

Embodiments of the presently disclosed surgical instrument including a jaw member, and methods of manufacturing thereof, are described in detail with reference to the drawings, in which like reference numerals designate identical or corresponding elements in each of the several views. As used herein the term "distal" refers to that portion of the surgical instrument and/or jaw member thereof, that is closer to the patient, while the term "proximal" refers to that portion of the surgical instrument and/or jaw member, that is farther from the patient.

Figure 1B:
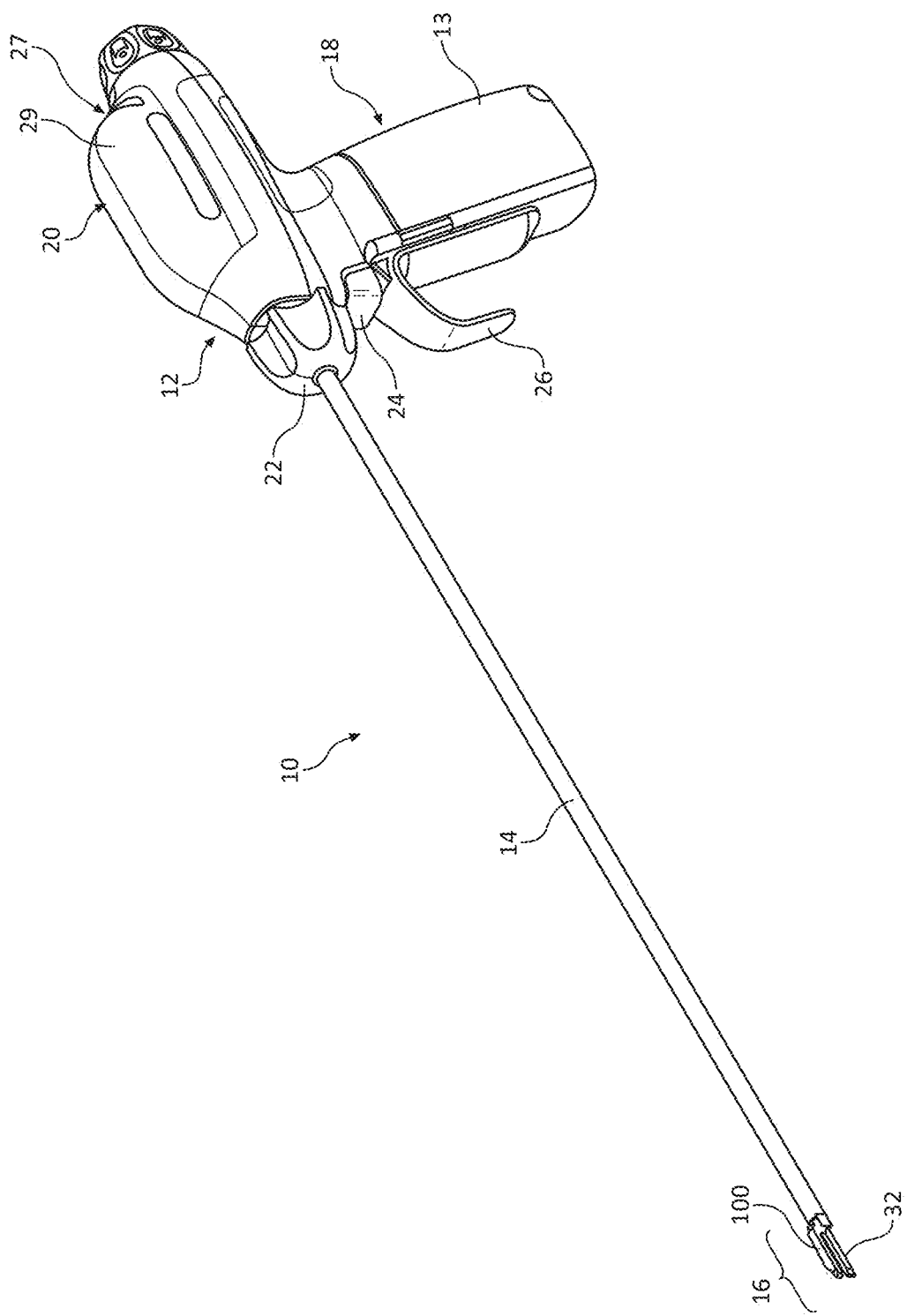
FIG. 1B is a perspective view of the ultrasonic surgical instrument of FIG. 1A, wherein the tool assembly is illustrated in a closed, clamping condition.
Figure 2:
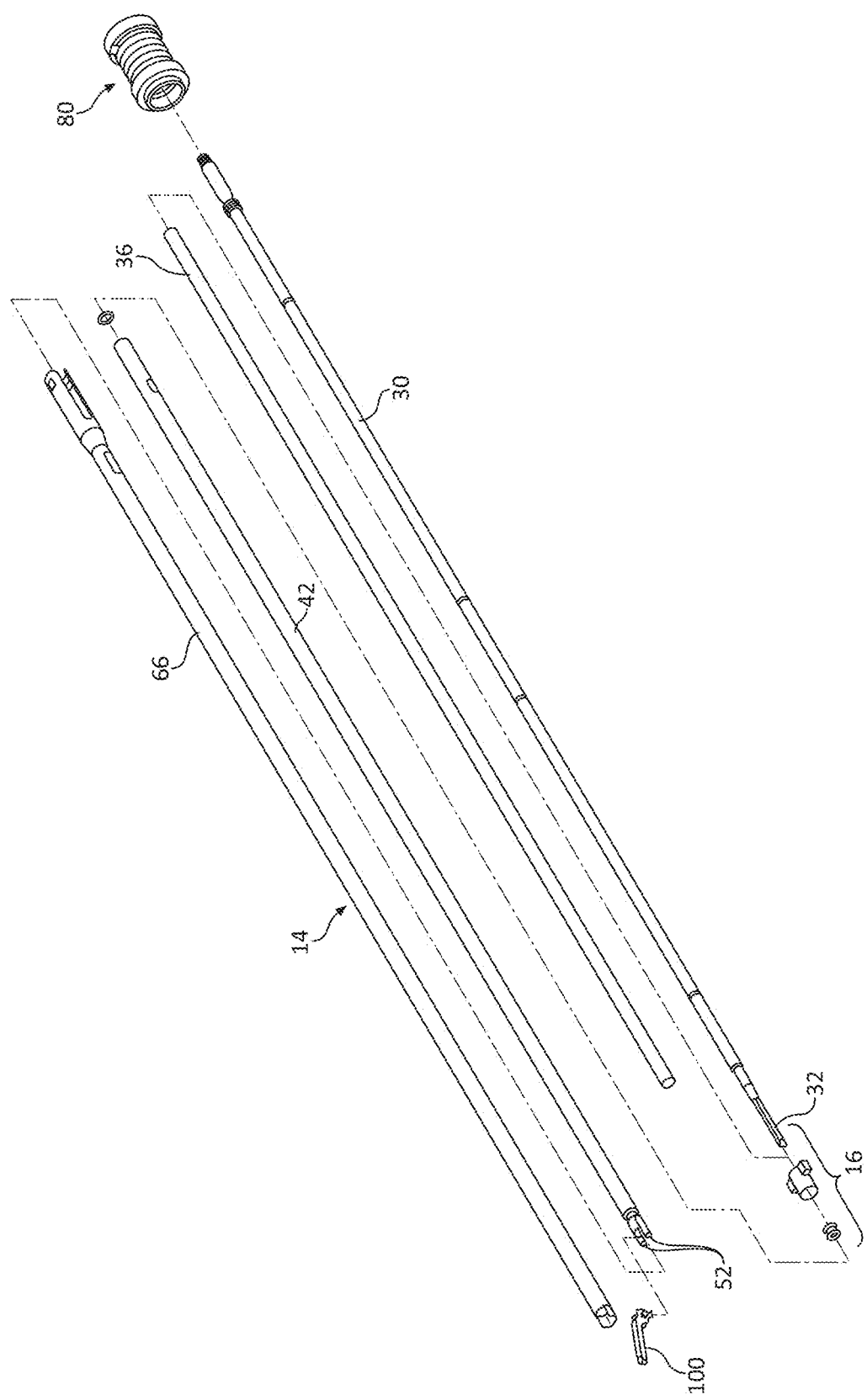
FIG. 2 is an exploded, perspective view of a shaft, a waveguide, and the tool assembly of the ultrasonic surgical instrument of FIG. 1A.

Referring generally to FIGS. 1A, 1B, and 2, an embodiment of an ultrasonic surgical instrument is shown and identified by reference numeral 10. As will be described in detail below, provided are jaw members for use with ultrasonic surgical instrument 10. The jaw members include a jaw support base and a jaw liner configured to fix the jaw liner within the jaw support base and inhibit detachment therefrom during use of ultrasonic surgical instrument 10. It is contemplated that the various jaw members detailed herein may also be used with other surgical instruments other than ultrasonic surgical instrument 10, for example, any suitable type of surgical instrument that functions to grasp, cut, dissect, and/or clamp tissue, such as any suitable electromechanical surgical instrument or electrosurgical instrument. For the purposes herein, ultrasonic surgical instrument 10 is generally described.

Ultrasonic surgical instrument 10 generally includes a handle assembly 12, an elongated body portion 14, and a tool assembly 16. Tool assembly 16 includes a blade 32 and a clamp member or jaw member 100. Handle assembly 12 supports a battery assembly 18 and an ultrasonic transducer and generator assembly ("TAG") 20, and includes a rotatable nozzle 22, an activation button 24, and a clamp trigger 26. Battery assembly 18 and TAG 20 are each releasably secured to handle assembly 12, and are removable therefrom to facilitate disposal of the entire device, with the exception of battery assembly 18 and TAG 20. However, it is contemplated that any or all of the components of ultrasonic surgical instrument 10 be configured as disposable single-use components or sterilizable multi-use components.

Elongated body portion 14 of ultrasonic surgical instrument 10 includes a waveguide 30 which extends distally from handle assembly 12 to tool assembly 16. A distal end of waveguide 30 defines blade 32 of tool assembly 16. A proximal end of waveguide 30 is configured to engage TAG 20. Elongated body portion 14 of ultrasonic surgical instrument 10 includes an isolation tube 36 positioned about waveguide 30 to prevent the transfer of ultrasonic energy from waveguide 30 to an inner support tube 42 of elongated body portion 14. Waveguide 30 and inner support tube 42 are rotatably coupled to rotatable nozzle 22 such that rotation of nozzle 22 effects corresponding rotation of inner support tube 42 and waveguide 30. Elongated body portion 14 further includes an actuator tube 66 coupled to inner support tube 42 and configured to rotate upon rotation of nozzle 22.

Inner support tube 42 of elongated body portion 14 is positioned about isolation tube 36 and includes a distal end having a pair of spaced clamp support arms 52. Spaced clamp support arms 52 are configured to pivotally engage pivot members 102 (FIG. 3) formed on jaw member 100 of tool assembly 16 to enable pivoting of jaw member 100 between an open position (FIG. 1A), in which jaw member 100 is spaced from blade member 32, and a closed position (FIG. 1B), in which jaw member 100 is approximated relative to blade member 32. Jaw member 100 is moved between the open and closed positions in response to actuation of clamp trigger 26.

Outer actuator tube 66 of elongated body portion 14 is slidably supported about inner support tube 42 and is operably coupled to jaw member 100 such that jaw member 100 is pivoted from the open position (FIG. 1A) to the closed position (FIG. 1B) as actuator tube 66 is slid about inner support tube 42 between an advanced position and a retracted position. A proximal end of outer actuator tube 66 is operably coupled with rotatable nozzle 22 such that outer actuator tube 66 is rotatably secured to, and slidable relative to, rotatable nozzle 22. The proximal end of outer actuator tube 66 is also operably coupled with a drive mechanism 80.

Handle assembly 12 includes drive mechanism 80 supported therein for linear movement relative to handle assembly 12. Handle assembly 12 also includes the aforementioned clamp trigger 26, which is operably coupled with drive mechanism 80 such that, in use, when clamping trigger 26 is compressed towards battery assembly 18 (FIG. 1B), outer actuator tube 66 is moved from the advanced position to the retracted position to pivot jaw member 100 from the open position to the closed position in relation to blade 32.

Battery assembly 18 is connected to a lower end of handle assembly 12 to define a fixed handgrip portion of handle assembly 12 and includes an outer housing 13. TAG 20 includes a generator 27 and an ultrasonic transducer (not explicitly shown). Generator 27 includes an outer housing 29.

In general, in use, when battery assembly 18 and TAG 20 are attached to handle assembly 12 and waveguide 30, respectively, and ultrasonic surgical instrument 10 is activated, battery assembly 18 provides power to generator 27 of TAG 20 which, in turn, uses this power to apply an AC signal to the ultrasonic transducer of TAG 20. The ultrasonic transducer, in turn, converts the AC signal into high frequency mechanical motion. This high frequency mechanical motion produced by the ultrasonic transducer is transmitted to blade 32 via waveguide 30 for application of such ultrasonic energy to tissue adjacent to or clamped between blade 32 and jaw member 100 of tool assembly 16 to treat the tissue.

Figure 3:
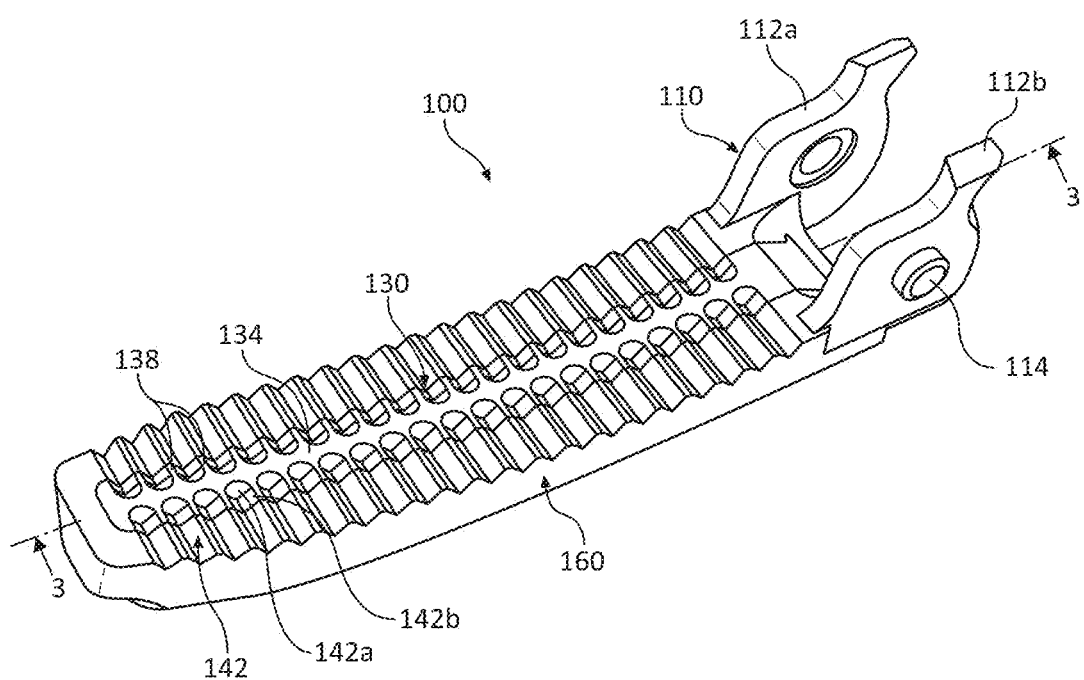
FIG. 3 is an enlarged perspective view of a jaw member for use with the ultrasonic surgical instrument of FIG. 1A.
Figure 4:
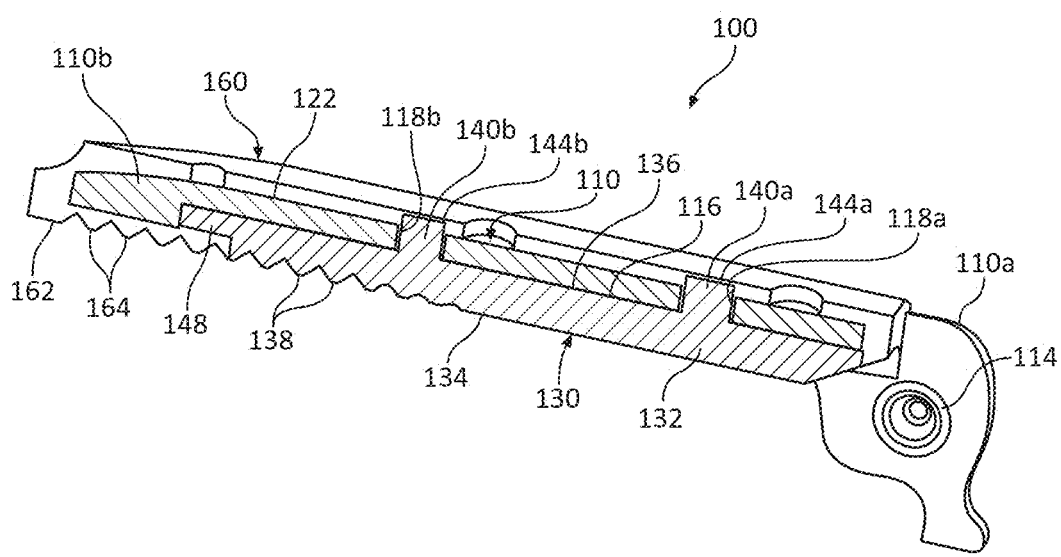
FIG. 4 is an enlarged longitudinal, cross-sectional view taken along section line 4-4 of FIG. 3.

With reference to FIGS. 3 and 4, an embodiment of a jaw member 100 configured for use with a surgical instrument, for example, ultrasonic surgical instrument 10 described above, is illustrated. Jaw member 100 generally includes a support frame or support base 110, a jaw liner 130, and a jaw overmold 160. Support base 110 of jaw member 100 has a relatively rigid construction to provide integrity to jaw member 100 such that jaw member 100 applies pressure to tissue when tool assembly 16 is in the clamped configuration (FIG. 1B). Support base 110 may be fabricated from a metal-containing material, for example, steel or any other suitable material, and may be machined, stamped, metal injection molded, or formed via any other suitable process.

Support base 110 has a generally elongated configuration and defines a longitudinal axis. It is contemplated that support base 110 may have a linear configuration along the longitudinal axis or a curvilinear configuration. Support base 110 has a proximal portion 110a and a distal portion 110b. Proximal portion 110a of support base 110 has a pair of spaced-apart, proximally extending flanges 112a, 112b. Flanges 112a, 112b each have a connector, for example, a boss 114 configured for pivotable receipt in a correspondingly shaped recess (not explicitly shown) defined in spaced clamp support arms 52 (see FIG. 2) of ultrasonic surgical instrument 10. As such, when flanges 112a, 112b of support base 110 are coupled to spaced clamp support arms 52 of ultrasonic surgical instrument 10 (see FIG. 2), jaw member 100 is pivotable relative to blade 32 of ultrasonic surgical instrument 10 to selectively clamp tissue between jaw member 100 and blade 32 (see FIGS. 1A and 1B).

Support base 110 of jaw member 100 defines a channel or cavity 116 therein that extends longitudinally along proximal and distal portions 110a, 110b thereof. Channel 116 is configured for receipt of jaw liner 130 of jaw member 100, as will be described in detail below. Support base 110 further defines a pair of longitudinally-spaced, transversely-extending apertures 118a, 118b therethrough. In some embodiments, support base 110 may include any suitable number of apertures defined therethrough. It is further contemplated that apertures 118a, 118b may extend only partially through the thickness of support base 110 rather than entirely therethrough. Apertures 118a, 118b are in communication with channel 116 of support base 110 and have a cylindrical configuration. In some embodiments, apertures 118a, 118b may assume a variety of shapes, such as, for example, squared, triangular, key-shaped, or the like.

With continued reference to FIGS. 3 and 4, jaw liner 130 of jaw member 100 is fabricated from a compliant material that allows blade 32 of ultrasonic surgical instrument 10 (see FIG. 2) to vibrate while in contact therewith without causing damage to blade 32 or other components of ultrasonic surgical instrument 10, and without compromising the hold on tissue grasped therebetween. Jaw liner 130 is configured to be situated in support base 110 along the longitudinal axis of support base 110 such that blade 32 makes contact with jaw liner 130 rather than support base 110 when tool assembly 16 is in the clamped condition (FIG. 1B). Jaw liner 130 may be fabricated from a plastic, for example, polytetrafluoroethylene, polyetheretherketone, perfluoroalkoxy, and/or fluorinated ethylene propylene. In some embodiments, jaw liner may be fabricated from any suitable compliable material, for example, soft metals, rubbers, or the like.

Jaw liner 130 of jaw member 100 generally includes an elongate body 132, and a pair of projections 140a, 140b extending transversely from a bottom surface 136 of elongate body 132. Elongate body 132 of jaw liner 130 is configured for receipt in channel 116 of support base 110, and has a top or tissue-contacting surface 134 and the bottom surface 136. Tissue-contacting surface 134 of jaw liner 130 has a plurality of teeth 138 disposed along a length of jaw liner 130. Teeth 138 have a trapezoidal shape, but it is contemplated that teeth 138 may assume and suitable shape that functions to aid in grasping or holding tissue between jaw member 100 and blade 32 (FIG. 2). Teeth 138 are arranged on tissue-contacting surface 134 in first and second spaced-apart rows disposed in parallel relation with one another. Tissue-contacting surface 134 of jaw liner 130 defines a space 142 between adjacent teeth 138. Spaces 142 each have an arcuate portion 142a disposed adjacent a central longitudinal axis of tissue-contacting surface 134, and a triangular portion 142b in communication with arcuate portion 142a.

Projections 140a, 140b of jaw liner 130 are configured for receipt in respective apertures 118a, 118b of support base 110. Projections 140a, 140b extend transversely from bottom surface 136 of elongate body 132 at a substantially perpendicular angle relative to elongate body 132. In some embodiments, projections 140a, 140b may extend at any suitable angle relative to bottom surface 136 of elongate body 132. Projections 140a, 140b are longitudinally spaced from one another, and have a cylindrical configuration corresponding to the cylindrical configuration of apertures 118a, 118b of support base 110. In some embodiments, projections 140a, 140b may assume any suitable shape configured to secure or retain projections 140a, 140b of jaw liner 130 within respective apertures 118a, 118b of support base 110. When jaw liner 130 is pressed into channel 116 of support base 110, projections 140a, 140b of jaw liner 130 extend through apertures 118a, 118b of support base 110 and project to or from a bottom surface 122 of support base 110 to expose an end 144a, 144b of each projection 140a, 140b.

With continued reference to FIGS. 3 and 4, jaw overmold 160 of jaw member 100 may be fabricated from a moldable plastic material suitable to withstand high temperatures generated in jaw member 100 during use of ultrasonic surgical instrument 10. For example, jaw overmold 160 may be fabricated from moldable fluoropolymers, moldable perfluoroether, polytetrafluoroethylene, or fluorinated ethylene propylene. Jaw overmold 160 is overmolded onto support base 110 and jaw liner 130 to fix jaw liner 130 to support base 110.

Jaw overmold 160 has a tissue contacting surface 162 that defines a U-shaped configuration, surrounding and being flush with tissue-contacting surface 134 of jaw liner 130. Tissue-contacting surface 162 of jaw overmold 160 has teeth 164, similar to teeth 138 of jaw liner 130 described above. Jaw overmold 160 and jaw liner 130 are designed such that when jaw overmold 160 is assembled with support base 110 and jaw liner 130, teeth 164 of jaw overmold 160 and teeth 138 of jaw liner 130 are continuous with one another.

To assemble or manufacture jaw member 100, jaw liner 130 is seated within channel 116 of support base 110 so that projections 140a, 140b of jaw liner 130 are positioned within respective apertures 118a, 118b of support base 110. With jaw liner 130 temporarily, but firmly secured to support base 110, jaw overmold 130 is overmolded onto support base 110 and jaw liner 134. In particular, jaw overmold 130 covers bottom surface 122 of support base 110 and ends 144a, 144b of projections 140a, 140b, and wraps around distal portion 110b of support base 110 while also covering a distal tip 148 of jaw liner, securing jaw liner 130 within channel 116 of support base 110. Once jaw member 100 is assembled or manufactured, jaw member 100 may be pivotably connected to elongated body portion 14 (FIG. 2) of ultrasonic surgical instrument 10.

Figure 5:
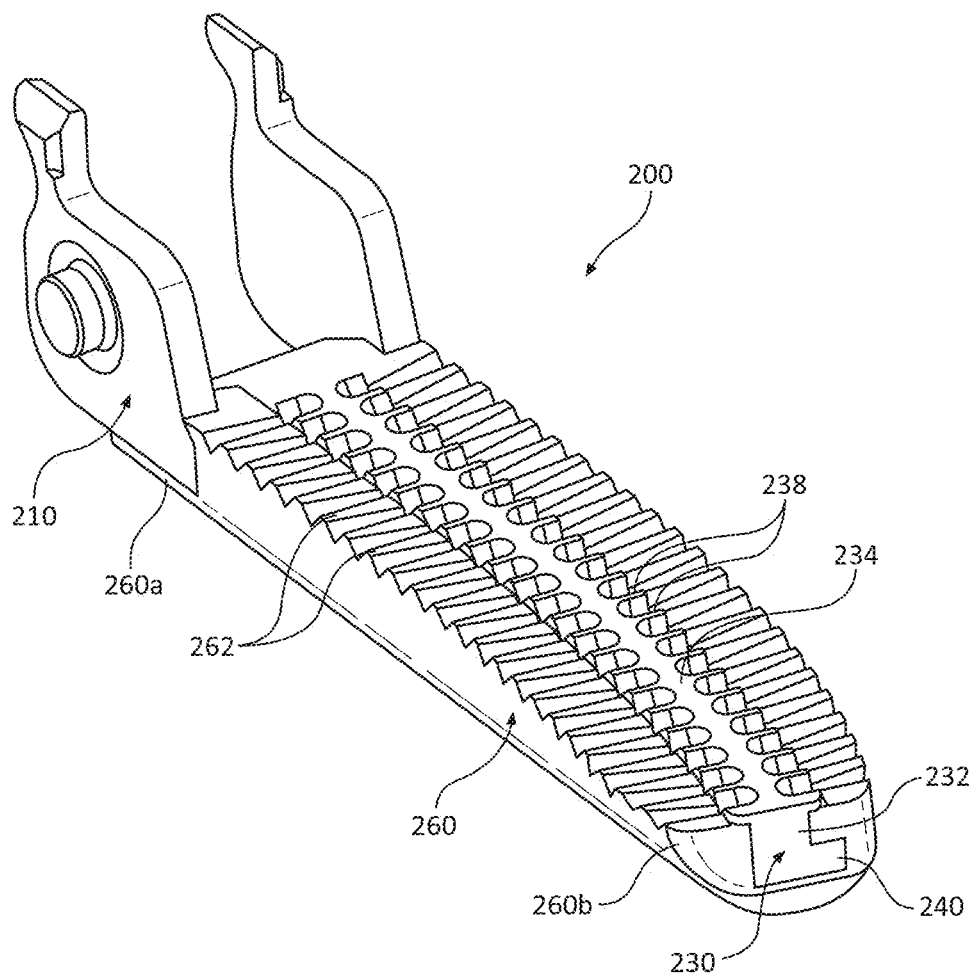
FIG. 5 is an enlarged perspective view of another jaw member for use with the ultrasonic surgical instrument of FIG. 1A.
Figure 6:
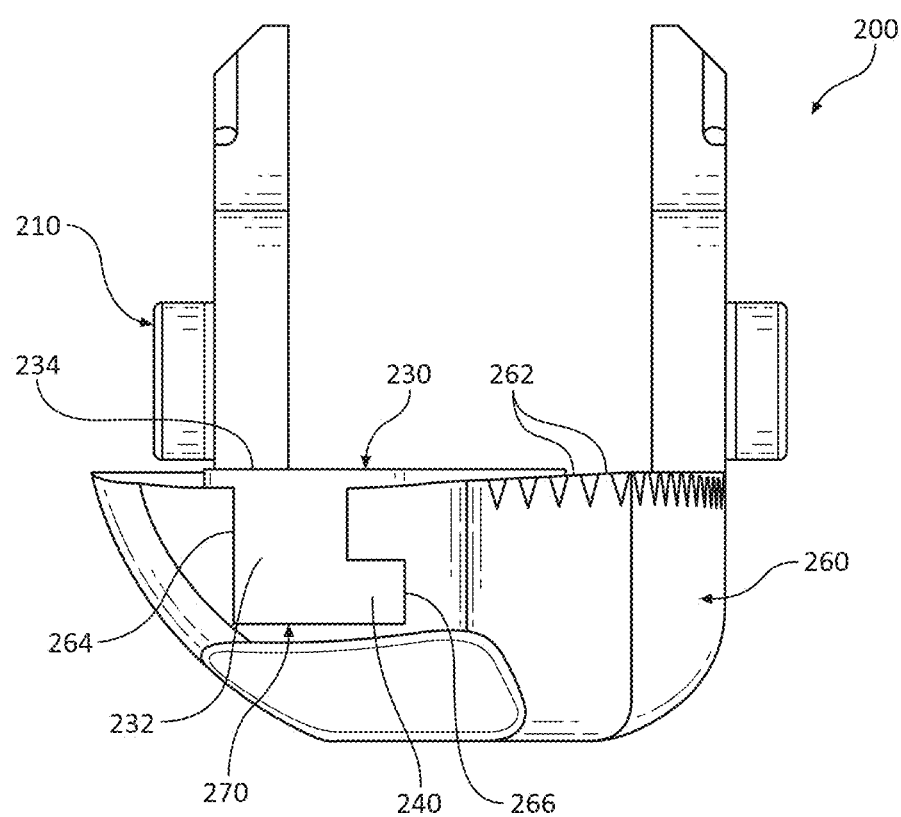
FIG. 6 is an enlarged front view of the jaw member of FIG. 5.
Figure 7:
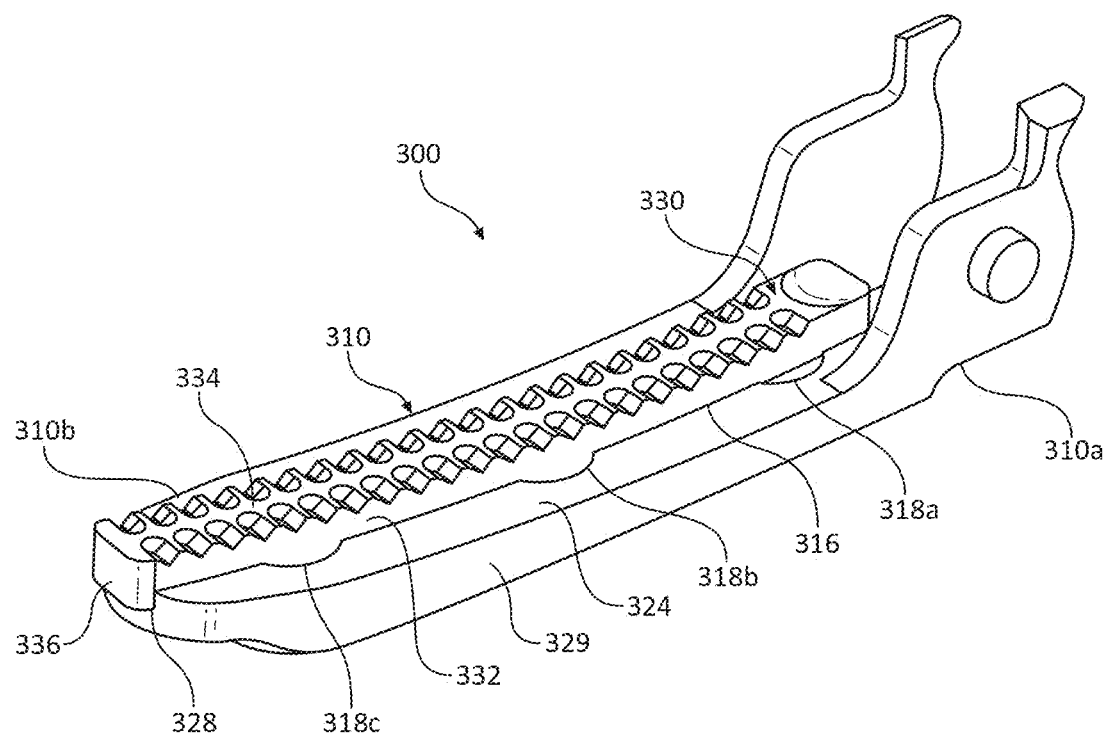
FIG. 7 is an enlarged perspective view from one side of another jaw member for use with the ultrasonic surgical instrument of FIG. 1A.
Figure 8:
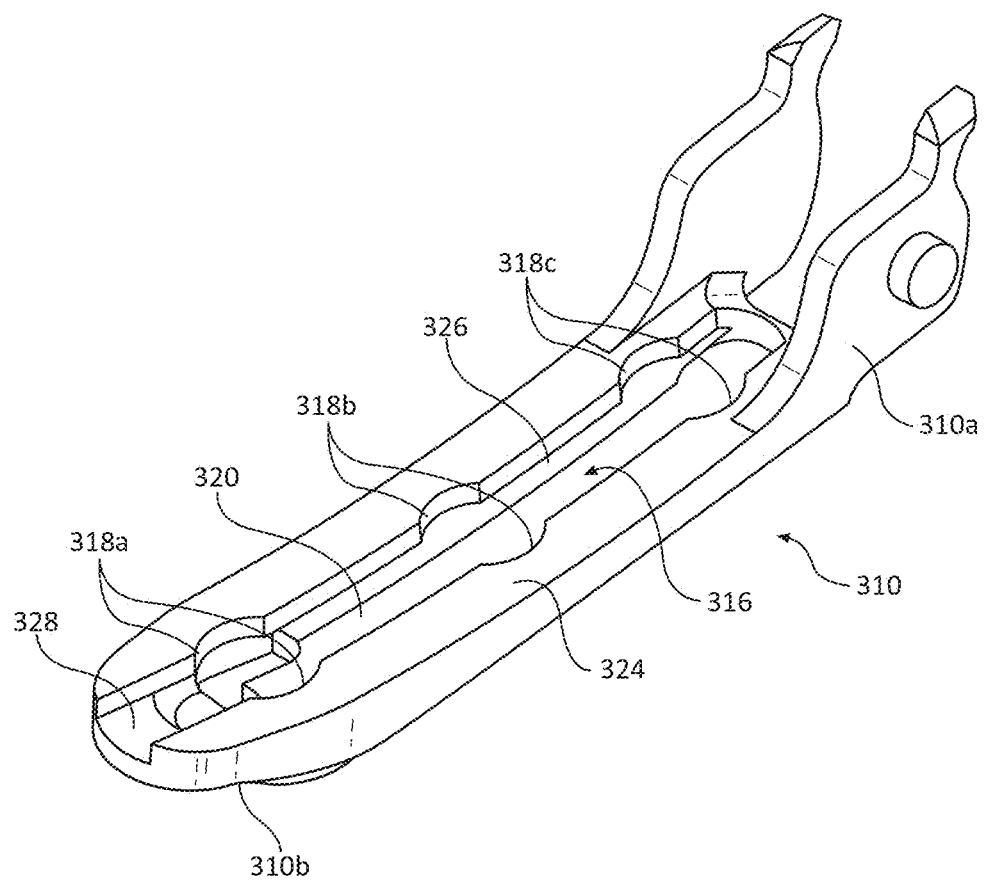
FIG. 8 is an enlarged perspective view of a support base of the jaw member of FIG. 7.
Figure 9:
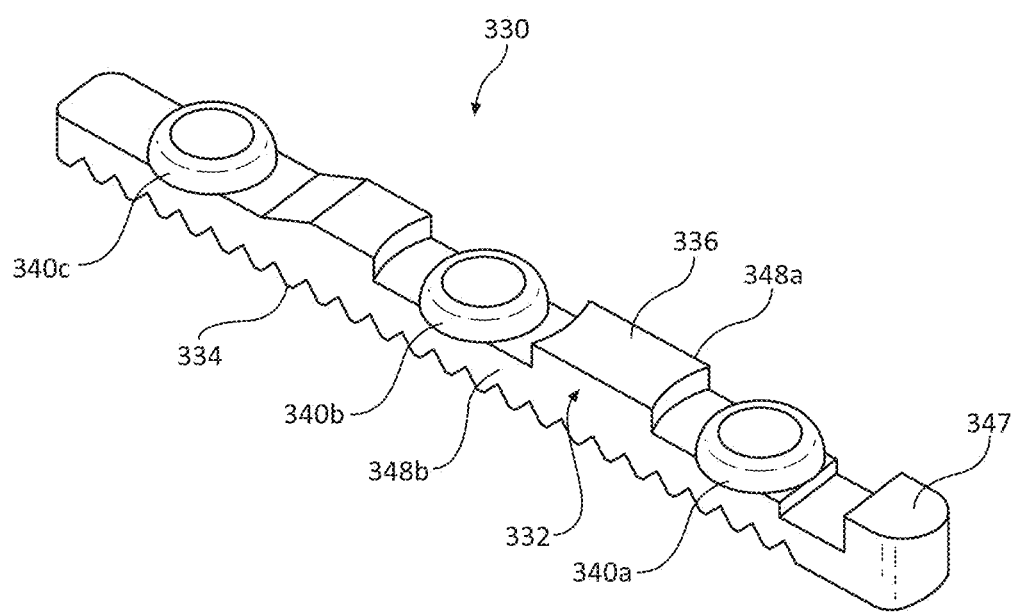
FIG. 9 is an enlarged perspective view of a jaw liner of the jaw member of FIG. 7.
Figure 10:
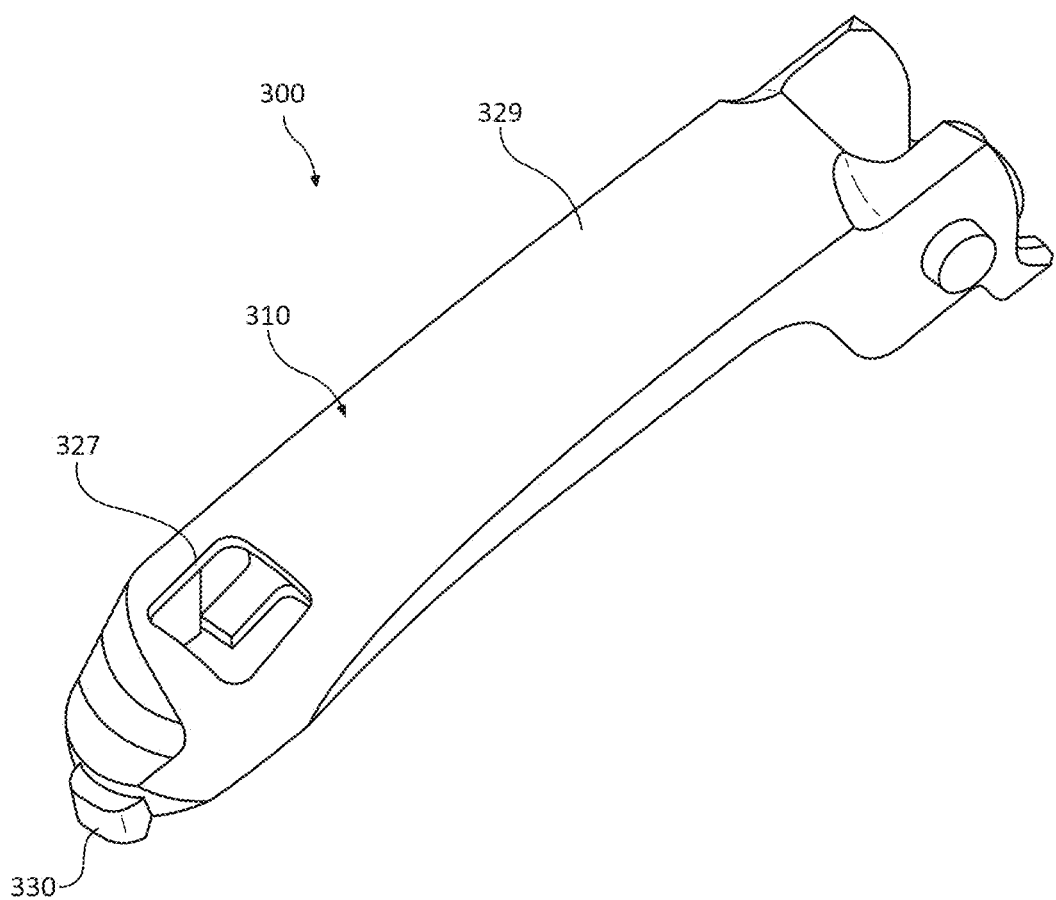
FIG. 10 is an enlarged perspective view from the other side of the jaw member of FIG. 7.

With reference to FIGS. 5 and 6, another embodiment of a jaw member 200 configured for use with ultrasonic surgical instrument 10 is illustrated. Jaw member 200 is similar to jaw member 100 described above with reference to FIGS. 3 and 4. Thus, to prevent unnecessary repetition, only differences between the embodiments are described. Jaw member 200 generally includes a support base 210, a jaw liner 230, and a jaw overmold 260.

Jaw liner 230 of jaw member 200 includes an elongate body 232, an appendage 240 extending from elongate body 232, and a tissue-contacting surface 234 defined on elongate body 232. Elongate body 232 of jaw liner 230 is configured for receipt in support base 210, and has a rectangular configuration, although other suitable configurations are also contemplated. Appendage 240 of jaw liner 230 extends laterally from a side of elongate body 232 at a substantially perpendicular angle relative to elongate body 232. Appendage 240, like elongate body 232, has a rectangular configuration such that elongate body 232 and appendage 240 together give jaw liner 230 an L-shaped transverse cross-sectional profile. Elongated body 232 and appendage 240 are configured for receipt in support base 210. Support base 210, more specifically, may define a channel (not shown) configured to receive at least a portion of elongated body 232 and appendage 240, and may be configured to receive elongated body 232 and appendage 240 via distal sliding of jaw liner 230 or transverse insertion so as to engage jaw liner 230 with support base 210 via compression fitting.

Tissue-contacting surface 234 of jaw liner 230 has a plurality of teeth 238 disposed along a length of jaw liner 230, and may define a width greater than that of elongated body 232 of jaw liner 230. Tissue-contacting surface 234 of jaw liner 230 may further be configured such that tissue-contacting surface 234 projects from a top surface 262 of jaw overmold 260, rather than being continuous therewith as with jaw liner 130 and jaw overmold 160 (FIGS. 3-4). However, a continuous configuration is also contemplated. Top surface 262 of jaw overmold 260 and tissue-contacting surface 234 of jaw liner 230 may define non-planar, for example, concave configurations.

Jaw overmold 260 of jaw member 200 is formed about support base 210, elongated body 232, and appendage 240 of jaw liner 230. More specifically, jaw overmold 260 is formed to define a channel 264 that extends longitudinally between proximal and distal portions 260a, 260b thereof and an aperture 266 that extends longitudinally between proximal and distal portions 260a, 260b of jaw overmold 260. Channel 264 and aperture 266 cooperatively form an elongated cavity 270. Channel 264 has a rectangular configuration, and aperture 266 has a rectangular configuration such that elongated cavity 270 of jaw overmold 260 has an L-shaped transverse cross-sectional profile corresponding to jaw liner 230. When jaw overmold 260 is formed about support base 210 and jaw liner 230, jaw liner 230 is disposed within cavity 270 of jaw overmold 260 with elongate body 232 residing within channel 264 and appendage 240 residing within aperture 266, thus securing jaw liner 230, support base 210, and jaw overmold 260 relative to one another.

To assembly or manufacture jaw member 200, jaw liner 230 is disposed within support base 210 as noted above and jaw overmold 260 is overmolded about support base 210 and jaw liner 230 to secure jaw liner 230, support base 210, and jaw overmold 260 to one another. Once jaw member 200 is assembled or manufactured, jaw member 200 may be pivotably connected to elongated body portion 14 (FIG. 2) of ultrasonic surgical instrument 10.

With reference to FIGS. 7-10, another embodiment of a jaw member 300 configured for use with ultrasonic surgical instrument 10 is illustrated. Jaw member 300 is similar to jaw member 100 described above with reference to FIGS. 3 and 4. Thus, to prevent unnecessary repetition, only differences between the embodiments are described. Jaw member 300 includes a support base 310, a jaw liner 330, and a jaw overmold (not explicitly shown, similar to jaw overmolds 160, 260 (FIGS. 3 and 5, respectively)). Support base 310 of jaw member 300 defines a channel 316 therein that extends longitudinally between proximal and distal portions 310a, 310b thereof. Channel 316 extends through a top surface 324 of support base 310 and only partially through a thickness of support base 310 to form an inner surface 320 of support base 310 that is recessed relative to top surface 324. Channel 316 is configured for receipt of jaw liner 330, as will be described in detail below.

Support base 310 further defines a series of longitudinally spaced apertures 318a, 318b, 318c that extend from either side of channel 316. Apertures 318a-c are in communication with channel 316 of support base 310. Each aperture 318a-c is formed by a portion of channel 316 and arcuate cutouts on opposite sides of channel 316. In some embodiments, apertures 318a-c may assume a variety of shapes, such as, for example, squared, triangular, key-shaped, or the like. Support base 310 further defines an inner groove 326 along the periphery of channel 316, and a notch 328 in distal portion 310b of support base 310.

Jaw liner 330 of jaw member 300 includes an elongate body 332 and a series of projections 340a, 340b, 340c extending transversely from elongate body 332. Elongate body 332 of jaw liner 330 is configured for receipt in channel 316 of support base 310. Jaw liner 330 has a bottom surface 336 and a top or tissue-contacting surface 334.

Projections 340a-c of jaw liner 330 extend downward from bottom surface 336 of jaw liner 330 at a substantially perpendicular angle relative to elongate body 332. Projections 340a-c are longitudinally spaced from one another, and each has a mushroom-shaped configuration corresponding to the arcuate configuration of apertures 318a-c of support base 310. In some embodiments, projections 340a-c may assume any suitable shape that secures or retains projections 340a-c of jaw liner 330 within respective apertures 318a-c of support base 310. Projections 340a-c have a diameter so as to protrude laterally beyond first and second sides 348a, 348b of elongate body 332. Projections 340a-c have a diameter greater than apertures 318a-c of support base 310 such that when jaw liner 330 is pressed into channel 316 of support base 310, projections 340a-c of jaw liner 330 flex to allow for projections 340a-c to pass through apertures 318a-c and then flex back to their original configuration upon being seated within inner groove 326 of support base 310 to retain jaw liner 330 within channel 316 in compression-fit engagement therewith.

Jaw liner 330 further includes a distal foot 347 that is configured for receipt within notch 328 of distal portion 310b of support base 310, e.g., via compression-fit.

To assemble or manufacture jaw member 300, projections 340a-c of jaw liner 330 are aligned with respective apertures 318a-c of support base 310 and distal foot 347 is aligned with notch 328. Thereafter, jaw liner 330 is pressed into channel 316 of support base 310. As jaw liner 330 is pressed into support base 310, projections 340a-c of jaw liner 330 engage top surface 324 of support base 310 causing projections 340a-c to flex due to the rounded or tapered edges of projections 340a-c. With projections 340a-c in a flexed state, projections 340a-c pass through apertures 318a-c of support base 310 until projections 340a-c are disposed within inner groove 326 of support base 310, allowing projections 340a-c to expand back towards their original, non-flexed state. Further, distal foot 347 is pressed into notch 328.

Projections 340a-c are prevented from backing out of apertures 318a-c since the diameter of projections 340a-c is greater than the diameter of apertures 318a-c. However, it is contemplated that jaw liner 330 may be removed from channel 316 of support base 310 using an access hole 327 (see FIG. 10) defined in a bottom surface 329 of support base 310. In particular, a blunt object, for example, may be passed through access hole 327 to apply a threshold amount of pressure on jaw liner 330 to dislodge jaw liner 330 from support base 310.

With jaw liner 330 secured to support base 310, a jaw overmold (not explicitly shown) may be overmolded onto support base 310 and jaw liner 330 to cover apertures 318a-c of support base 310, thereby securing jaw liner 330 to support base 310. It is contemplated that the jaw overmold may cover distal ends of support base 310 and jaw liner 330 to more securely fix jaw liner 330 with support base 310 and, further may fill the remainder of access hole 327 to also aid in securely fixing jaw liner with support base 310. The jaw overmold may be configured similarly to jaw overmold 160 (FIG. 3) or jaw overmold 260 (FIG. 5) or any other suitable overmold. Once jaw member 100 is assembled or manufactured, jaw member 300 may be pivotably connected to elongated body portion 14 (FIG. 2) of ultrasonic surgical instrument 10.

Figure 11A:
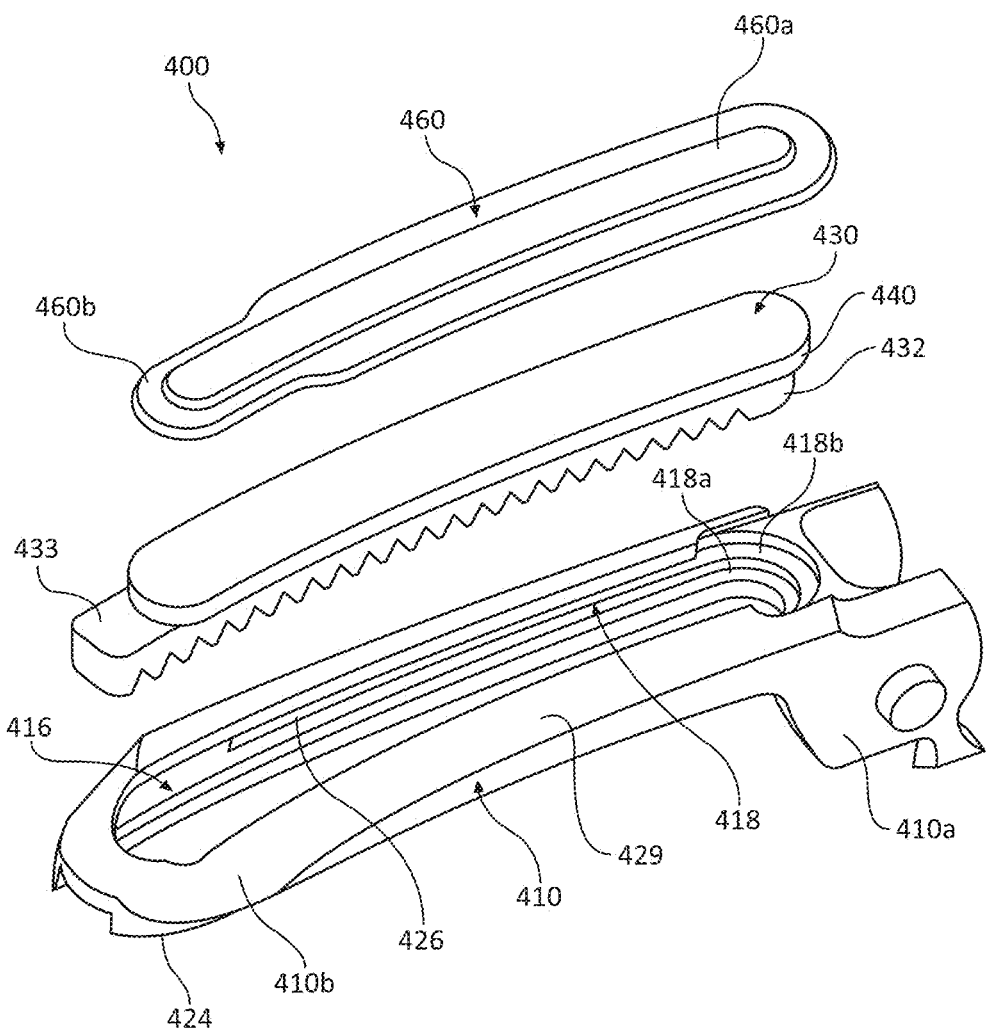
FIG. 11A is an exploded, perspective view from one side of another jaw member for use with the ultrasonic instrument of FIG. 1A.
Figure 11B:
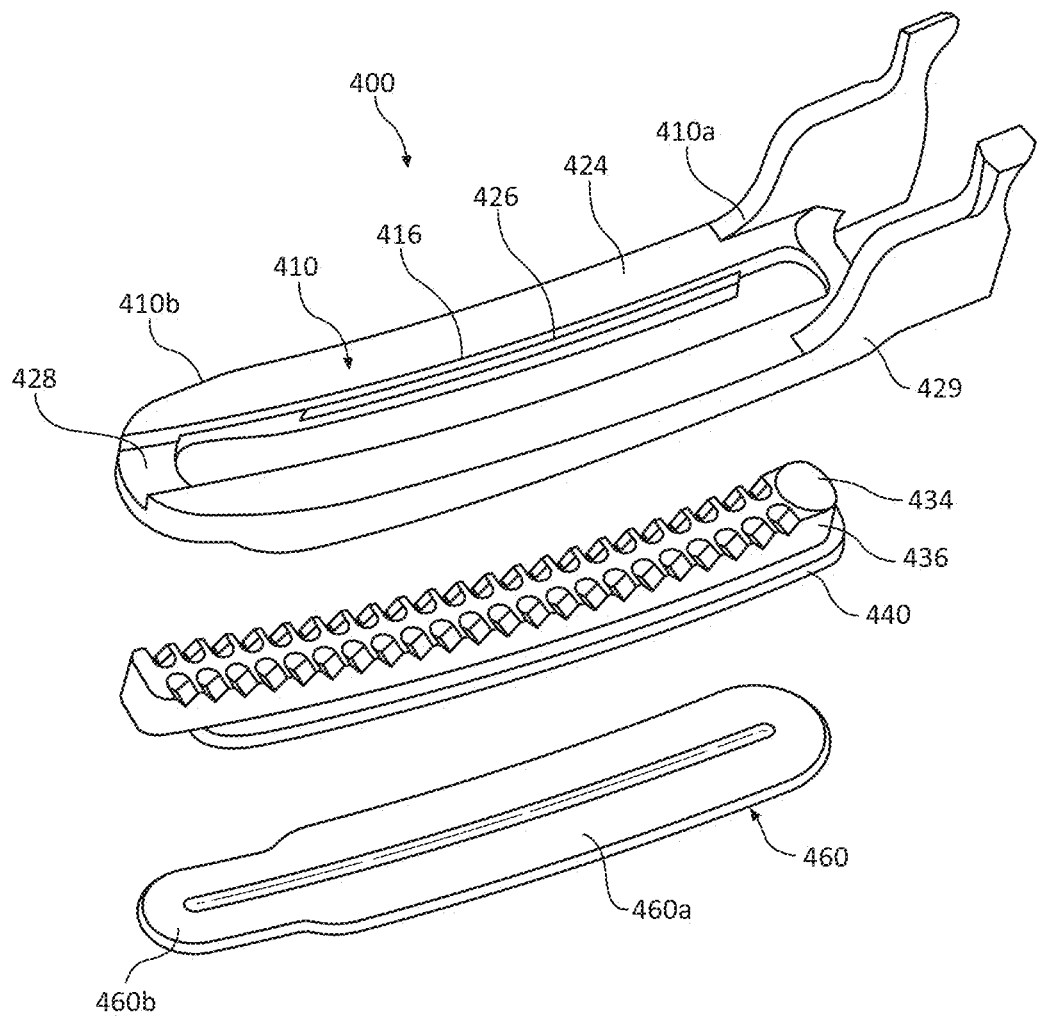
FIG. 11B is an exploded, perspective view from the other side of the jaw member of FIG. 11A.
Figure 11C:
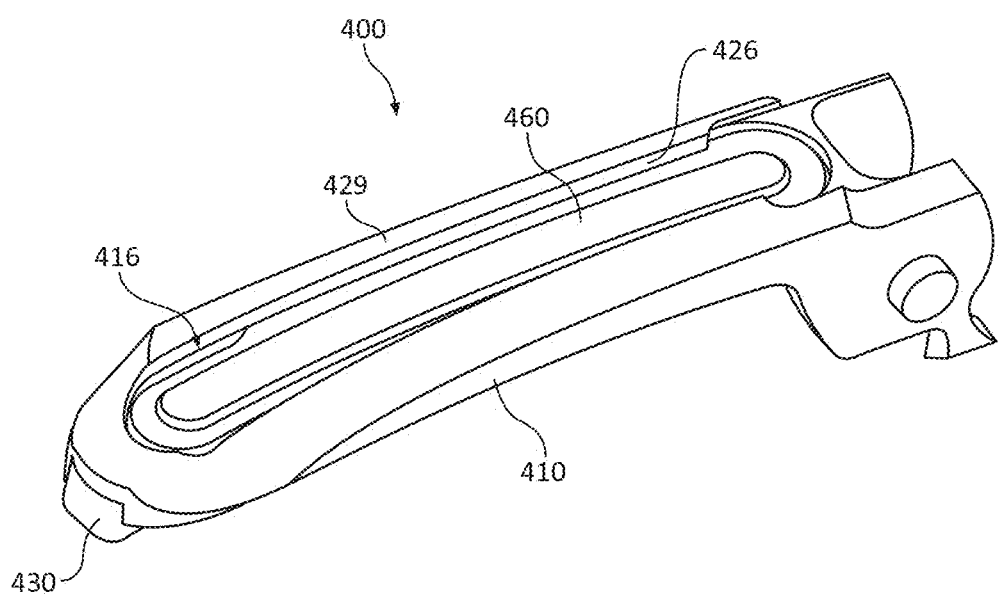
FIG. 11C is a perspective view of the jaw member as illustrated in FIG. 11A, with parts assembled.

With reference to FIGS. 11A-11C, another embodiment of a jaw member 400 configured for use with ultrasonic surgical instrument 10 is illustrated. Jaw member 400 is similar to jaw member 100 described above with reference to FIGS. 3 and 4. Thus, to prevent unnecessary repetition, only differences between the embodiments are described. Jaw member 400 includes a support base 410, a jaw liner 430, and an elongated plate 460.

Support base 410 of jaw member 400 defines a channel 416 therein that extends longitudinally between proximal and distal portions 410a, 410b thereof. Channel 416 extends through a top surface 424 of support base 410, a thickness of support base 410, and a bottom surface 429 of support base 410. Channel 416 is configured for receipt of jaw liner 430 and jaw overmold 460, as will be described in detail below. Support base 410 includes a stepped portion 418 therein that outlines channel 416. Stepped portion 418 defines a first ledge 418a and a second ledge 418b, each of which being oriented towards bottom surface 429 of support base 410.

Bottom surface 429 of support base 410 extends over second ledge 418b to define an inner groove 426 between second ledge 418b and bottom surface 429. Inner groove 426 is configured for slidable receipt of plate 460, in a proximal-to-distal direction. Distal portion 410b of support base 410 defines a notch 428 therein that only extends partially through the thickness of support base 410 and which is configured for receipt of a distal portion of jaw liner 430, as will be described in detail below.

Jaw liner 430 of jaw member 400 includes an elongate body 432 and a projection 440. Elongate body 432 has a rectangular configuration defining a bottom surface 436 and a top surface or tissue-contacting surface 434. Projection 440 has an elliptical configuration and is disposed on bottom surface 436 of elongate body 432. Projection 440 extends radially outward from a periphery of elongate body 432. Projection 440 is configured to be disposed on first ledge 418a of support base 410 while a distal tip 433 of elongate body 432 is configured to be disposed in a notch 428 defined in distal portion 410b of support base 410.

With continued reference to FIGS. 11A-11C, elongated plate 460 of jaw member 400 has a proximal portion 460a configured similarly to projection 440 of jaw liner 430, and a distal portion 460b configured similarly to elongate body 432 of jaw liner 430. Proximal portion 460a of plate 460 is configured to be disposed on second ledge 418b of support base 410 and to cover jaw liner 430. Bottom surface 429 of support base 410 prevents plate 460 from passing transversely out of channel 416 of support base 410, while jaw liner 430 is configured to be capable of being passed transversely into support base 410 from the bottom side thereof.

To assemble or manufacture jaw member 400, jaw liner 430 is inserted, from the bottom side of support base 410, into channel 416 of support base 410 such that projection 440 of jaw liner 430 is positioned on first ledge 418a of support base 410 and distal tip 433 of jaw liner 430 is positioned in notch 428 of support base 410. Notch 428 prevents jaw liner 430 from sliding longitudinally relative to support base 410 and first ledge 418a prevents jaw liner 430 from moving transversely out of channel 416 through top surface 424 of support base 410. The relative configuration of jaw liner 430 and support base 410 prevents side-to-side movement of jaw liner 430 once disposed within support base 410. Plate 460 is slid longitudinally into channel 416 of support base 410 to position the periphery of plate 460 within groove 426 of support base 410 while laying plate 460 on second ledge 418b of support base 410. With plate 460 positioned on jaw liner 430 and captured between bottom surface 429 of support base 410 and second ledge 418b of support base 410, plate 460 prevents jaw liner 430 from backing out of support base 410 through bottom surface 429 of support base 410. Plate 460, jaw liner 430, and support base 410 may further be configured such that plate 460 retains jaw liner 430 in position via compression-fit. In some embodiments, a jaw overmold (not shown) may be applied to top surface 424 of support base 410 to aid in securing jaw liner 430 to support base 410. Once jaw member 400 is assembled or manufactured, jaw member 400 may be pivotably connected to elongated body portion 14 (FIG. 2) of ultrasonic surgical instrument 10.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A jaw member for use with a surgical instrument, the jaw member comprising:
    a support base having a proximal portion configured to be pivotably coupled to a surgical instrument, and a distal portion, the support base defining a channel that extends longitudinally between the proximal and distal portions and an aperture disposed in communication with the channel;
    a jaw liner including an elongate body configured for receipt in the channel of the support base, and a projection extending from the elongate body and configured for receipt in the aperture of the support base; and
    wherein the distal portion of the support base defines a notch therein configured for receipt of a distal tip of the elongate body of the jaw liner; and
    a jaw overmold that covers at least one outer lateral side of the support base and at least one lateral side of the jaw liner to fix the jaw liner to the support base.

2. The jaw member according to claim 1, wherein the jaw overmold includes a top surface having a plurality of teeth configured to contact tissue.

3. The jaw member according to claim 2, wherein the jaw liner has a non-planar tissue-contacting surface, and the top surface of the jaw overmold is non-planar.

4. The jaw member according to claim 1, wherein the jaw liner has a tissue-contacting surface fabricated from a plastic.

5. The jaw member according to claim 4, wherein the plastic is selected from the group consisting of polytetrafluoroethylene, polyetheretherketone, perfluoroalkoxy, and fluorinated ethylene propylene.

6. The jaw member according to claim 1, wherein the jaw liner has a tissue-contacting surface having a plurality of teeth disposed along a length of the jaw liner.

7. The jaw member according to claim 6, wherein the plurality of teeth are arranged in two parallel rows.

8. The jaw member according to claim 7, wherein the tissue-contacting surface of the jaw liner defines a space between adjacent teeth of the plurality of teeth, the space having a triangular portion and an arcuate portion in communication with the triangular portion.

9. The jaw member according to claim 1, wherein the elongate body has a top surface configured to face tissue, and a bottom surface, the projection of the jaw liner extending radially outward from the bottom surface of the elongate body.

10. A jaw member for use with a surgical instrument, the jaw member comprising:
    a support base having a proximal portion configured to be pivotably coupled to a surgical instrument, and a distal portion, the support base defining a channel therein that extends longitudinally between the proximal and distal portions, the support base having a top surface, and a bottom surface defining an opening in communication with the channel, the top surface configured to face a first direction toward tissue and the bottom surface configured to face a second direction, opposite the first direction;
    a jaw liner including:
        an elongate body configured for receipt in the channel of the support base via the opening in the bottom surface of the support base; and
        a projection extending radially outward from a periphery of the elongate body and configured to be seated within the support base; and
    an elongated plate configured to cover the opening in the bottom surface of the support base and be coupled to the support base at a location adjacent the jaw liner to secure the jaw liner relative to the support base.

11. The jaw member according to claim 10, wherein the support base includes a stepped portion formed therein, the stepped portion defining a first ledge configured to receive the projection, and a second ledge configured to receive the plate.

12. The jaw member according to claim 11, wherein the bottom surface extends over the second ledge such that the plate is captured between the bottom surface of the support base and the second ledge of the support base.

13. The jaw member according to claim 10, wherein the distal portion of the support base defines a notch therein configured for receipt of a distal tip of the elongate body of the jaw liner.

14. A jaw member for use with a surgical instrument, the jaw member comprising:
    a support base having a proximal portion configured to be pivotably coupled to a surgical instrument, and a distal portion, the support base defining a channel therein that extends longitudinally between the proximal and distal portions, the support base having a top surface, and a bottom surface defining an opening in communication with the channel, the top surface configured to face a first direction toward tissue and the bottom surface configured to face a second direction, opposite the first direction; and
    a jaw liner including:
        an elongate body configured to be at least partially received in the channel of the support base via the opening in the bottom surface of the support base and supported on the distal portion of the support base; and
        a projection extending from the elongate body and configured to be supported in the channel of the support base.

15. The jaw member according to claim 14, wherein the support base has a first ledge disposed within the channel, the projection of the jaw liner being supported on the first ledge.

16. The jaw member according to claim 14, wherein the projection extends radially outward from a periphery of the elongate body.

17. The jaw member according to claim 14, further comprising an elongated plate configured to be coupled to the support base at a location adjacent the jaw liner to secure the jaw liner relative to the support base.

18. The jaw member according to claim 17, wherein the support base defines an inner groove in communication with the channel, the inner groove configured to slidably receive the plate.

19. The jaw member according to claim 14, wherein the channel defines a closed proximal end.

20. The jaw member according to claim 14, wherein the channel defines closed proximal and distal ends.

* * * * *